US012567491B2

(12) United States Patent
Reid et al.

(10) Patent No.: US 12,567,491 B2
(45) Date of Patent: Mar. 3, 2026

(54) STORAGE DEVICES AND OPERATION METHODS THEREOF

(71) Applicant: FFF Enterprises, Inc., Temecula, CA (US)

(72) Inventors: Kenneth Shay Reid, Temecula, CA (US); Connor Ramm, Temecula, CA (US); Brandon Beckendorf, Temecula, CA (US)

(73) Assignee: FFF Enterprises, Inc., Temecula, CA (US)

( * ) Notice: Subject to any disclaimer, the term of this patent is extended or adjusted under 35 U.S.C. 154(b) by 55 days.

(21) Appl. No.: 18/409,495

(22) Filed: Jan. 10, 2024

(65) Prior Publication Data
US 2025/0226071 A1     Jul. 10, 2025

(51) Int. Cl.
| A61J 7/04 | (2006.01) |
| A61J 7/00 | (2006.01) |
| G06F 21/31 | (2013.01) |
| G16H 20/10 | (2018.01) |

(52) U.S. Cl.
CPC ............. G16H 20/10 (2018.01); G06F 21/31 (2013.01)

(58) Field of Classification Search
CPC ................................. G16H 20/10; G06F 21/31
See application file for complete search history.

(56) References Cited

U.S. PATENT DOCUMENTS

| 10,842,712 B1 * | 11/2020 | Wingate, III ............. A61J 1/03 |
| 11,126,955 B1 | 9/2021 | Watson et al. |
| 11,282,028 B2 | 3/2022 | Reid |
| 11,443,844 B2 | 9/2022 | Jeong |
| 2021/0224773 A1 | 7/2021 | Fazekas et al. |
| 2021/0241875 A1 * | 8/2021 | Rasmussen ........ G07C 9/00896 |

(Continued)

FOREIGN PATENT DOCUMENTS

| CN | 115303690 | 11/2022 |
| WO | 2021064691 | 4/2021 |
| WO | 2021170126 | 9/2021 |

OTHER PUBLICATIONS

Frontoni et al., "Information Management for Intelligent Retail Environment: The Shelf Detector System," Information, 5, pp. 255-271 (2014).

(Continued)

*Primary Examiner* — Maroun P Kanaan
(74) *Attorney, Agent, or Firm* — Fox Rothschild LLP

(57)     ABSTRACT

A flex weight sensing tray system for storing packaged medicine and regulated medical products for taking is disclosed. The system may include an integrated portable open-top tray, a platform having a weight sensing area and an optical scanner. The system may include computer readable instructions that cause a processor to store scanned information, authenticate user credentials, permit the user to enter a user selection to remove products from the tray, calculate a first weight and a second weight using the database and the one or more weight sensors, permit the user to obtain the products when it is determined that (a) the one or more serial numbers corresponds to the user selection and (b) a difference between the first weight and the second weight falls within a tolerance and update one or more product statuses in the database in order to track removal of items from the tray.

16 Claims, 7 Drawing Sheets

(56) References Cited

U.S. PATENT DOCUMENTS

| | | | |
|---|---|---|---|
| 2022/0108271 A1 | 4/2022 | Cui et al. | |
| 2022/0292446 A1 | 9/2022 | Teramoto | |
| 2022/0414595 A1 | 12/2022 | Adato et al. | |
| 2023/0021719 A1 | 1/2023 | Hahamy | |
| 2023/0177458 A1 | 6/2023 | Kim et al. | |
| 2024/0197569 A1 * | 6/2024 | Hoffman | A61J 7/0084 |
| 2024/0299256 A1 * | 9/2024 | Matamoros | A61J 7/0436 |

OTHER PUBLICATIONS

Saqlain et al., "Hybrid Approach for Shelf Monitoring and Planogram Compliance (Hyb-SMPC) in Retails Using Deep Learning and Computer Vision," Hindawi, Mathematical Problems in Engineering, vol. 2022, Article ID 4916818, 18 pages (2022).
WiiHeyTechnologies, "Smart Shelf-Management System for Retail," 4 pages, brochure available online <https://www.wiihey.com/en/applications/smart-shelf-management-system.html> (2018).

* cited by examiner

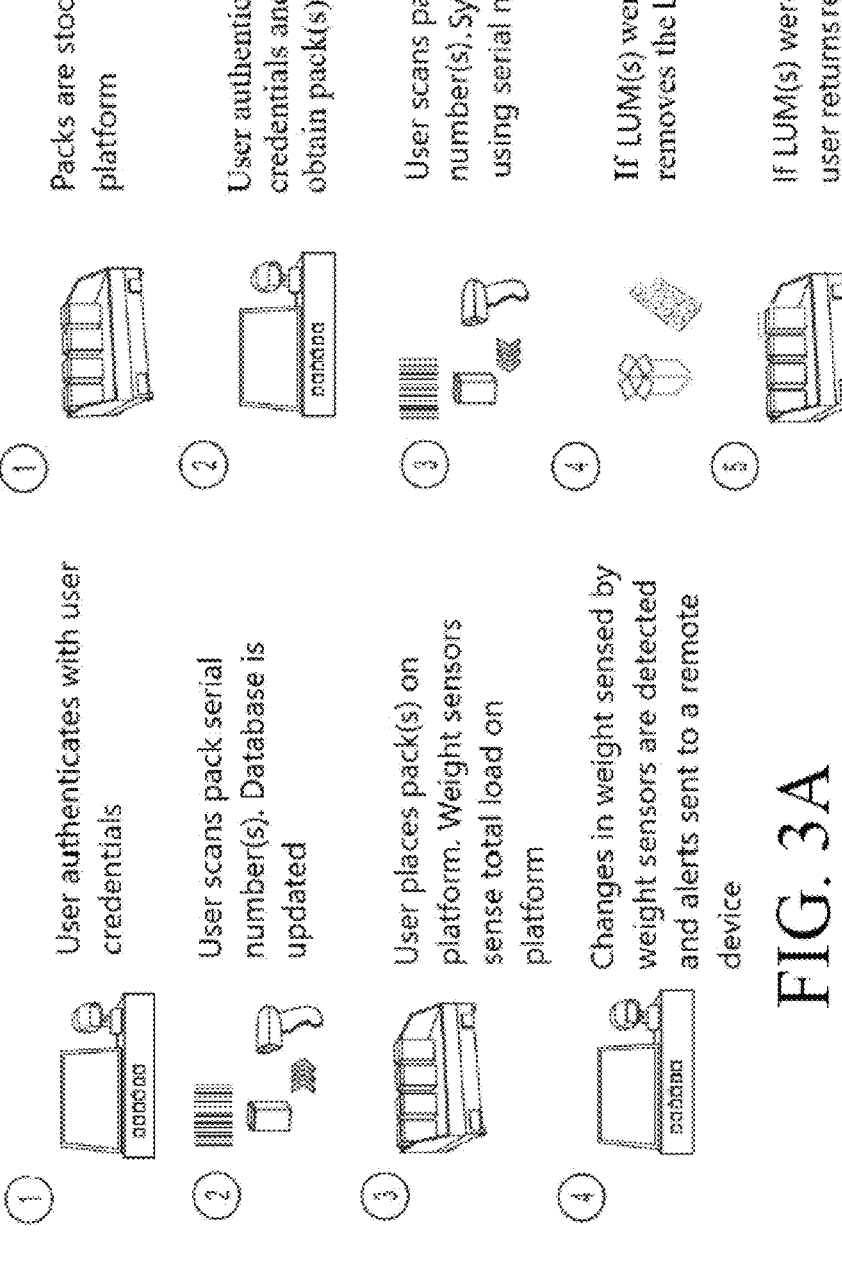

1. User authenticates with user credentials

2. User scans pack serial number(s). Database is updated

3. User places pack(s) on platform. Weight sensors sense total load on platform

4. Changes in weight sensed by weight sensors are detected and alerts sent to a remote device

FIG. 3A

1. Packs are stocked on the platform

2. User authenticates with user credentials and enters a selection to obtain pack(s) or LUM(s)

3. User scans pack or LUM serial number(s). System verifies pack or LUM using serial number and database 4. If LUM(s) were selected in step 2, user removes the LUM from pack 5. If LUM(s) were selected in step 2, user returns remaining LUM(s) to platform 6. System verifies that the correct pack(s) or LUM(s) were taken using database and weight sensor information

FIG. 3B

Systems Architecture:

STORAGE DEVICES AND OPERATION METHODS THEREOF

FIELD OF THE INVENTION

Embodiments of the present invention are related to platform type storage devices.

BACKGROUND OF THE INVENTION

In the field of medical facilities and treatment facilities, there is a general need and various methods for securely storing and tracking regulated, or controlled medical devices or medical treatments such as packaged pharmaceuticals. Regulated items may often times contain products that are harmful if mistakenly given to the wrong patient or can have consequences if stolen or misused. The items themselves can be under significant federal regulations directed to, for example, to controlling general public access. However, such products are often housed in these facilities on storage devices such as trays, tables and shelves, that are easily accessible, i.e., they are unlocked and in locations that many employees have access to meaning these regulated products are vulnerable to unauthorized access. Furthermore, often times the items are shipped to facilities in bulk packages. This creates potential for waste as facility employees may take possession of a bulk package in order to use only a portion of the bulk package. Additionally, because of the controlled nature of these items it is important to have a reliable method of tracking their chain of custody i.e. transfer between manufacturers, medical facilities and medical personnel. In some facilities or user applications, there are significant consequences or existing problems with inventory loss or mistakes. For example, in a hospital, loss of certain types of items can lead to significant financial loss and also raise safety issues. Mistakes can have significant consequences. Seeking to have precise tracking and security for items in such situations can have material advantages to those industries. Accordingly, there is a need in the industry for improved storage devices.

SUMMARY OF THE INVENTION

In one or more embodiments, a flex weight sensing tray system for packaged medicine and regulated medical products is provided. The system can include an integrated portable open-top tray comprising an enclosed housing and a platform positioned above housing, wherein the platform includes a solid flat surface that is adapted to receive and support a plurality of packaged medicine or regulated medical products. The platform can be adapted to be open for access by hand of a user so that a user can remove an item from the platform. The platform can include a weight sensing area with one or more weight sensors configured to sense the total load on the platform. The system can include an optical scanner configured to scan information such as a serial number from images or text such as 2D printed codes. The system can also include a processor, memory, wireless communications circuit and computer readable instructions stored in memory. The computer readable instructions cause the processor and wireless communications circuit to store scanned information, such as serial numbers and product codes, from one or more products, at both the bulk item level and at the individual item level, in a database, communicate to a user via a user interface the option to authenticate a set of credentials of the user, in response to authenticating the user, permit the user to enter a user selection via the user interface to remove one or more products from the tray, have the user scan the serial numbers of the removed product(s) with the optical scanner, calculate a first weight and a second weight using the database and the one or more weight sensors, permit the user interaction to obtain the one or more removed products to proceed without error when it is determined that (a) the one or more serial numbers corresponds to the user selection and (b) a difference between the first weight and the second weight falls within a tolerance and update one or more product statuses in the database in order to track removal of items from the tray.

In some embodiments, the database is stored on a remote server.

In some embodiments, the tray can include an enclosure that encloses the processor. In alternative embodiments, the processor can be located away from the tray in a tray management device, such as a tablet, computer, cellular phone or other remote device.

In some embodiments, the user interface can be located in the tray management device and in other embodiments the user interface may be located separately from the tray management device. The user interface can also be configured to display various messages or alerts to a user. For example, the user interface can be configured to communicate to the user whether an item is available, prompt the user to removed an item, prompt a user to scan an item, or alert the user that an item removed or scanned could not be verified and recommend an alternative action.

In some embodiments, the one or more product statuses includes an item count of the removed product(s).

In some embodiments the product codes can be a National Drug Code.

In some embodiments, the tolerance accounts for manuals, tools, packaging, and other items stored on the platform that are auxiliary to packaged medicine or regulated medical products. The tolerance can also account for the tare weight of the weight sensing area.

In some embodiments, the tray can include one or more walls enclosing the platform. These walls can, for example, aid in preventing products from falling off the platform.

In some embodiments, one of the one or more items removed is a first LUM from an unopened pack and at least one of the one or more statuses updated in the database is a count of LUMs remaining in the unopened pack following removal of the first LUM by a user.

In some embodiments, the system includes a temperature sensor configured to transmit a report on temperature to the processor.

In some embodiments, the database is configured to store information that facilitates tracking of the chain of custody of one or more products removed from the platform.

BRIEF DESCRIPTION OF THE DRAWINGS

FIG. 3A depicts a functional block diagram of a stocking procedure in accordance with some embodiments of the present invention.

FIG. 3B depicts a functional block diagram of a transfer procedure in accordance with some embodiments of the present invention.

DETAILED DESCRIPTION

The present application is related to a flex weight sensing tray system that stores items for later use. In some embodiments, technology described herein includes a portable open-top tray having a housing supporting a solid flat platform on which to store stocked items. The tray can be outfitted with one or more weight sensors that can sense the weight of the total load on the platform. The system can include an optical scanner configured to read text or images provided on the stored items. The system can include a processor, wireless communications circuit, memory and computer-readable instructions stored in memory and the processor can by way of the instructions direct the system to track the stored items as they are stocked and removed. The processor can be programmed with algorithms configured to detect information from one or more sensors such as a weight sensor or temperature sensor. A database can store item information such as information received from the optical scanner, item statuses, and information needed to track the chain of custody of the items. The system can also include a user interface by which to receive input from a user such as a user selection of items to remove. In addition, the user interface can be used to communicate to the user item information.

Figure 1A:
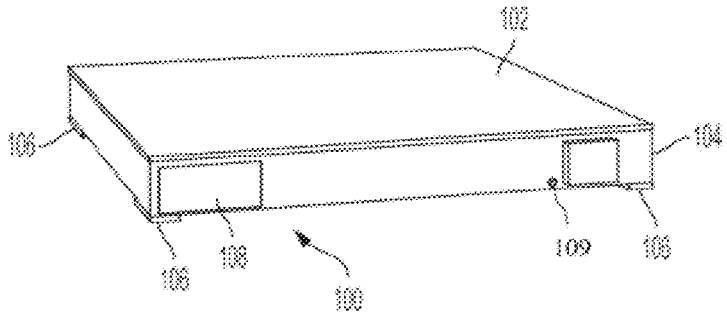
FIG. 1A depicts an illustrative tray in accordance with some embodiments of the present invention.
Figure 1B:
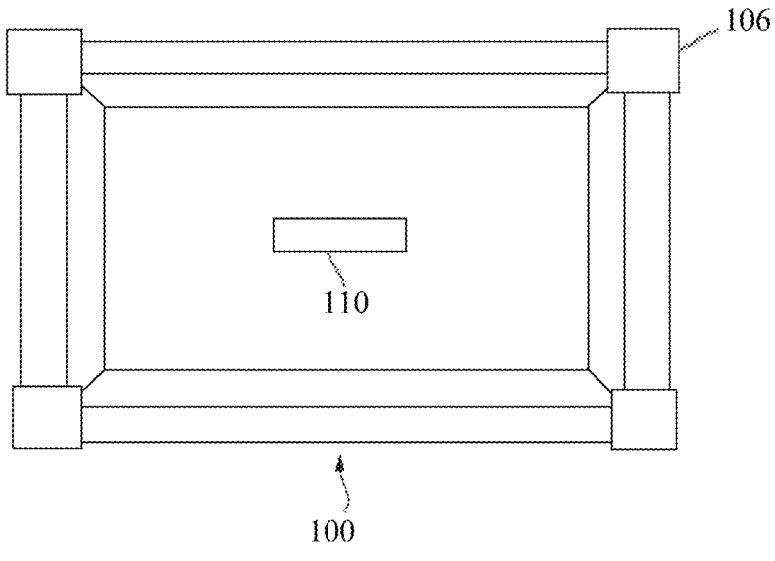
FIG. 1B depicts an alternative perspective of an illustrative tray in accordance with some embodiments of the present invention.

FIG. 1A illustrates a perspective view of a tray or tray device 100. Tray 100 includes legs 106 that are attached to the bottom of tray 100 to provide support for the tray 100. Tray 100 includes platform 102 that is adapted to be a physical platform adapted to carry the weight of or support products thereon as a source of product stock. Platform 102 is adapted to provide a flat plane that is to receive and support items that are placed on tray 100. The surface of the platform 102 is preferably a solid support surface that is rigid and provides a contiguous flat surface for receiving and supporting items thereon. As shown, the top surface is continuous flat to the edges without upward or downward slopes at the edges or throughout. Tray 100 is an open-top structure in that the top side of the tray is open for access by hand of user without any physical structures that block or interfere with free physical path of access by hand from the top to the top surface of the platform (regardless of whether a user is logged in or authenticated). Tray 100 may be adapted by way of a mechanical support to include a weight sensor 110, as shown in FIG. 1B, that generates an output signal that corresponds to the weight of one or more items sitting on a weight sensing area of the platform. Weight sensor 110 is affixed to platform 102 on the underside of the platform i.e., opposite the contiguous flat surface of platform 102 configured to receive items. However, weight sensor placements and configurations distinct from that shown in FIG. 1B are contemplated. Furthermore, the surface of the platform 102 is preferably configured to have the same level of height across the surface such as when an item is placed on the surface the underlying surface would be at the same level of the remaining surface (although in some embodiments the height of the overall platform may lower due to the weight but spots where items are places would not preferably compress). Tray 100 can include label or label area 108. Label area 108 can be configured to receive a printed label or a surface for writing an identification of the product stored on that tray 100. Tray 100 can also include an activation switch 109 on the front panel of the tray 100. As shown, tray 100 includes solid continuous side walls on the front, back and sides of the tray 100. The platform 102 and the front, back and side walls are adapted to form an enclosure within which the operational circuit and mechanical elements (if any) are positioned so as to be out of reach and sight. The enclosure provides security so as to prevent access to the internal operational aspects of the tray 100. Tray 100 can also include a bottom wall as part of the enclosure. Preferably, tray 100 is without a power switch for customer control over the power. If included, a power switch can be configured that is positioned on one of the walls that permits a user to have easy access from the wall to turn off the power to the tray 100. Tray 100 is preferably adapted to have a size and weight that is portable such that an individual can pick up and move the location of the tray to another tabletop or available shelf without difficulty. Preferably, tray 100 is adapted to operate as a wireless device meaning it does not have or require wires to connect the device to another device in order for it to be operating such as under normal conditions except with respect to a power cord in embodiments in which tray 100 is configured to connect with a power cord and power adapter (internal or external) to receive power from a wall outlet or other power source. In some embodiments, it is contemplated that it can be configured to include an internal battery such as a rechargeable battery that can be charged by a port on the tray 100 if desired, and it can communicate with other devices via wireless communications to perform its function within the inventory management and stocking system. In some embodiments, the tray can include one or more walls, not shown, collectively enclosing the platform in order to facilitate storage of items on the platform. The walls can be made of a transparent material and/or form an open top so that the items stored on the platform are visible. This configuration facilitates a user in quickly assessing the items on the platform and selecting, which can be beneficial during, for instance, a medical emergency.

Figure 2:
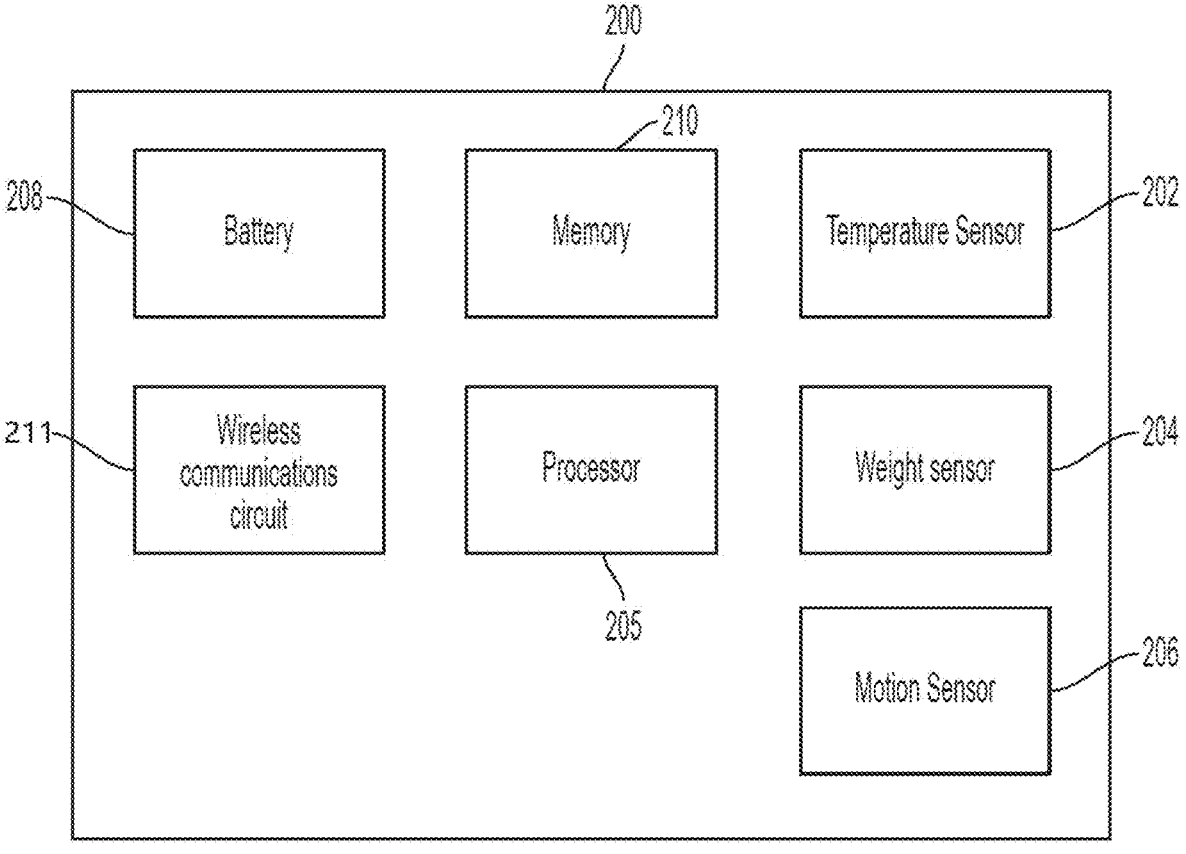
FIG. 2 depicts a functional block diagram of tray in accordance with some embodiments of the present invention.

FIG. 2 illustrates a functional block diagram of one embodiment of a tray or tray device 200 (tray device of FIG. 1A). The tray 200 includes a processor 205, memory 210 configured to store computer executable instructions, such as the algorithms described herein. The tray 200 can include a temperature sensor 202 that is configured to measure the temperature in the current environment in which tray 200 is positioned for service, a weight sensor 204 that is configured to measure the weight of items placed on the tray (e.g., using a load cell), and a motion sensor 206 that is configured to sense movement near the vicinity of the tray 200. Tray 200 may include battery 208 that is configured to supply power to tray 200 to be operational (run the processer, algorithm, sensors, etc.) Tray 200 can be configured to rely only on battery power and not contain any DC or AC voltage ports that connect to external power sources. As one option for additional complexity, tray 200 can include an integrated camera or have a camera that is connected by wire or wirelessly to tray 200 but a simple tray design without a camera is preferred.

In some embodiments, the temperature sensor 202 can be configured to sense temperature in the range of about 20 Celsius (C) to about 30 C. Additionally or alternatively, the system can be configured to alert a user if an item on the tray has not been stored under the recommended temperature conditions for a period of time sufficient to make the item "mishandled", "improperly stored" or to otherwise cause the item's safety and/or efficacy to become compromised. For example, the temperature sensor 202 can be configured to transmit to an external device, such as a tray management device or server, an update, wherein the update comprises a report on temperature. The temperature information in the update can be retrieved from memory 210 and/or from the temperature sensor 202 and communicated to the external device via wireless communications circuit 211. The external device can be configured with a database storing item information which can be updated based on the temperature update e.g. an item can be marked as unavailable if it was stored at an improper temperature. These updates can be sent periodically by the tray to the external device based on an algorithm stored in memory 210 and executed by the processor 205. Similarly, the system can be configured to send updates to a user or another device based on information from the weight sensor 204.

Memory 210, wireless communications circuit 211, weight sensor 204, temperature sensor 202, motion sensor 206, battery 208, can communicatively coupled to the processor 205 and can operate under the instructions of the processor 205.

The tray 200 may include wireless communication circuit 211. The wireless communication circuit 211 is configured to exchange data with an access point, a server, computer system, trays, or other connected devices via a communications network. Preferably, the wireless communication circuit 2101 is configured to implement communication exchange with a nearby tray management device (e.g. tablet, computer, cabinet or other electronic device). The tray management device may include a processor. The wireless communication circuitry 211 is operative to interface with a communications network using a suitable communications protocol such as WiFi, 802.11, Bluetooth, radio frequency systems such as 900 MHz, 1.4 GHz, and 5.6 GHz communication systems, infrared, GSM, GSM plus EDGE, CDMA, quadband, and other cellular protocols, or any other suitable protocol. Preferably, the wireless communication circuitry comprises low power and near field communications such as using Bluetooth. If desired, wireless communication circuit 211 can include an Ethernet adapter (for wired connection), a wireless network adapter, a Bluetooth adapter, or other similar types of adapters.

A tray or tray device including one or more of the components shown in FIG. 2 is contemplated.

The tray may include mechanical components that for example establish the capability to use the sensor to weight items placed on the tray. Tray 200 preferably includes an enclosure that encloses the operational circuitry and electronics (e.g., processor and memory) inside the enclosure. The enclosures secures the operational circuitry and electronics from being accessible. This protects from damage and unwanted access to the circuitry and electronics.

The tray 200 can be configured as part of a system that includes an optical scanner configured to scan information (e.g. a serial number) from items (by way of a barcode, QR code or other 2D printed code) to stock or remove items from inventory using the tray. The tray 200 may be implemented as one single device. Each component in the tray 200 may also be a separate, independent device and the components are connected together (e.g., through wireless connection) to form the functionality. Different combinations are also contemplated such that components can be removed or added in a broadening or narrowing way.

Figure 4:
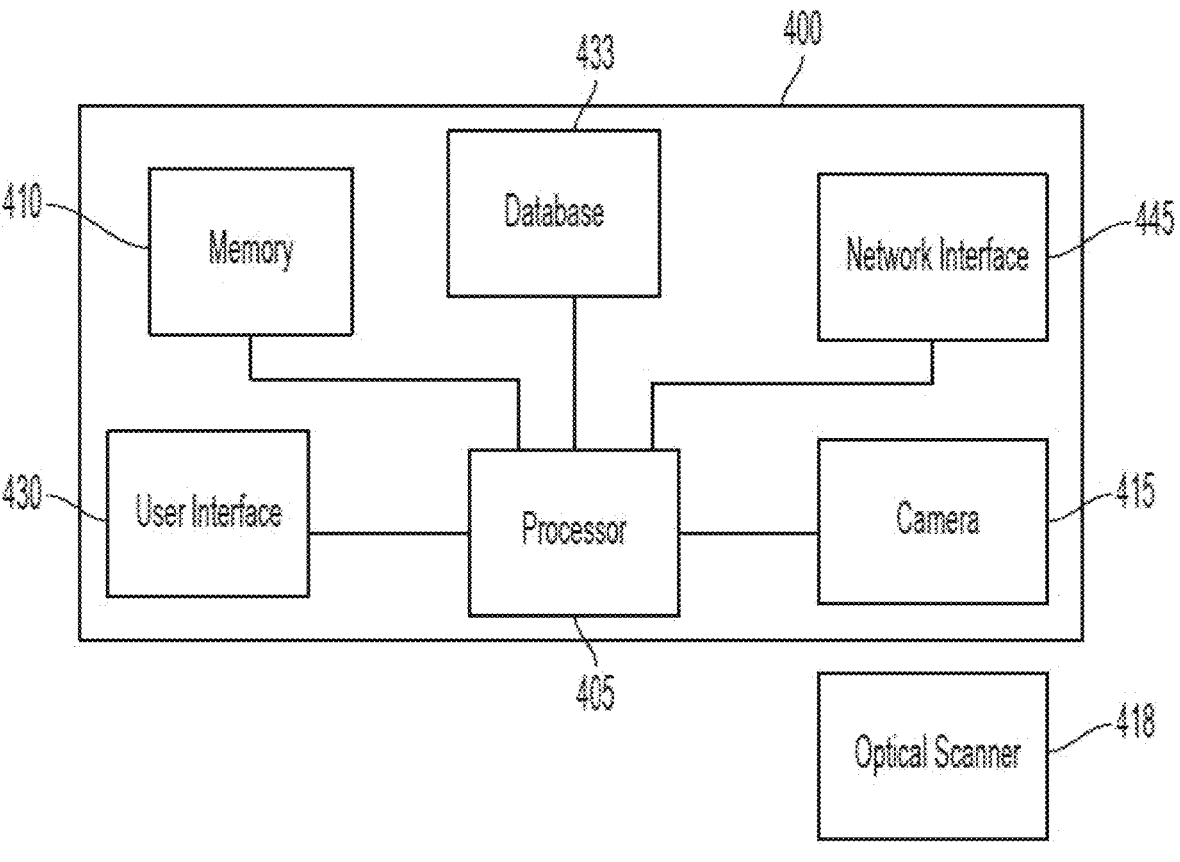
FIG. 4 depicts an illustrative functional block diagram of a tray management device in accordance with some embodiments of the present invention.

FIG. 4 illustrates a functional block diagram of one embodiment of a tray management device 400. The device 400 includes a processor 405, memory 410 configured to store computer executable instructions, such as the algorithms described herein, a user interface 430 configured to allow users to interact with the device 400, and a database 433. Database 433 can store product and item specific information that is used by the system in its operation processes. Database 433 can store data specific to each item stored on the tray including, without limitation, a serial number, a product code, a product name to which each item corresponds to provide a stock of that product on the tray, information identifying the tray in which the scanned item is stored (e.g. tray ID or room number), information identifying the personnel or facility in custody of the item, item count, manufacturer, date of manufacture, recommended storage conditions, date and time or storage and lot and expiration of the item if applicable. Database 433 can also store user authentication information, sensor readings, information for communicating between devices and other related information. The data can be added to or updated in the database as items are added and removed from the system. The information can be stored on a server and/or online application as opposed to locally or can be stored in combination.

Tray management device can include a camera 415 positioned and adapted to face the user and a view of the room where trays are positioned to record user interaction with the trays. If desired, device 400 can include a camera motor configured to control the movement of the camera 415. The device 400 may include additional cameras (e.g., the total number of cameras is three or more) and associated motors or may have only one camera. Memory 410, the camera 415, and the user interface 430, are communicatively coupled to the processor 405 and operate under the instructions of the processor 405. The camera 415 can also be communicatively coupled to processor 405. The camera 415 is preferably a visible light camera that primarily uses visible light to form an image (or frame in a video). A visible light camera, for example, can be a color camera (or color video camera) or a monochrome camera (or monochrome video camera). The device may be a physical structure such as box or computer enclosure that has camera 415 mounted on or inside it. One of more of the cameras can be an integrated component of a display monitor being used for the user interface. If desired, the camera can be positioned away from the box or computer enclosure and connected via a wired or wireless connection. The user interface 430 include devices that allow an individual to interact with the storage device. The user interface 430 may include a display, touch screen, mouse, keyboard, click wheel, trackball, keypad, button, dial, speaker, microphone, biometric reader, or any combination thereof. The user interface 430 includes devices that can receive input from the individual, and the input can be in the form of physical movement (touching or clicking the user interface 430) or audio (e.g., individual speaking to the user interface 430). Preferably, the user interface 430 includes a touch-sensible screen that presents an interactive graphical user interface to the current user of the storage device. The graphical user interface can be implemented using software (stored in non-transient memory), a processor (one or more), and memory. From the user interface 430 the user can enter a user selection identifying a quantity of items to remove. The user interface 430 can also provide information about the storage device. For example, the user interface 430 can notify individuals that a certain item is available or unavailable. The user interface 430 can also notify the user if they have removed the correct item from the storage device i.e. that the item removed corresponds to the user selection or satisfies another layer of authentication such as one that uses the change in total load on the platform.

The device 400 (or the storage device) may also include a network interface 445. The network interface 445 is configured to exchange data with an access point, a server, one or more trays, another computer system, trays, medical cabinet systems, or storage devices via a communications network. The network interface 445 is operative to interface with a communications network using a suitable communications protocol such as Wi-Fi, 802.11, Bluetooth, radio frequency systems such as 900 MHz, 1.4 GHz, and 5.6 GHz communication systems, infrared, GSM, GSM plus EDGE, CDMA, quadband, and other cellular protocols, or any other suitable protocol. The network interface 445 can include an Ethernet adapter (for wired connection), a wireless network adapter, a Bluetooth adapter, or other similar types of adapters. The network interface 445 can be communicatively coupled to the processor 405.

A tray management device including one or more of the components shown in FIG. 4 is also contemplated.

The tray management device 400 may include mechanical components such as for raising or lowering a display monitor.

The tray management device 400 can include or be associated with an optical scanner 418 that is configured with the device to scan items to stock or remove items from inventory.

The device 400 may be implemented as one single system. Each component in the system 400 may also be a separate, independent device and the components are connected together (e.g., through wireless connection) to form the device 400. Different combinations are also contemplated such that components can be removed or added in a broadening or narrowing way.

As shown in FIG. 4 and other FIGS., the tray management device is configured to be a physical station that is not a mobile device and is configured to sit on a counter as the location for its operation (generally fixed location). In preferred embodiments, the tray management device is a computer tablet such as an iPad or Android tablet that is configured using software to perform the functionality described herein. The computer tablet can be configured to include an optical scanner to scan codes. The computer tablet is a mobile device that has a physical configuration similar to the display screen shown in the figures for the tray management device. The profile and shape of tablets are generally known to those of ordinary skill in the art. The tablet implementation may include one or more cameras that are configured to face the user and a camera facing away from the user. The user-facing camera can be used to identify and store images or recordings of the user interacting with the tablet. The tablet can be generally placed near the vicinity of the trays so that different users can pick up the tablet and login and use the system. In such configuration, the tablet would not typically be configured to record video of users interacting with a platform to remove an item. If desired, this feature can be integrated with other cameras (e.g., wirelessly) in the room to generate such recording. Images or videos can be stored locally on the device, the tablet, or sent to be stored over a wide area network or LAN in some other location for retrieval and/or review. In such implementations, there could be a separate scanner that works with the tablet but preferably the tablet provides the functionality. Except as noted, the tablet preferably has the features and functionality illustratively described in connection with FIG. 4. The tray management device as described can include a tablet (or other mobile device) implementation. In other embodiments, the tray management device can be incorporated into a medical cabinet or medical cabinet system.

Memory can be tangible or intangible memory which can be used to carry or store desired program codes in the form of computer-executable instructions or data structures. Tangible memory, for example, may include random access memory, read only memory, magnetic disk storage media, optical storage media, flash memory devices, and other tangible and non-transitory storage devices. Intangible memory, for example, may include storages implemented by software.

Database can also be tangible or intangible databases which can be used to carry or store storage device data, administrator and user data, or other high-level data generated as a result of executing the computer instructions in the memory (other than computer instructions themselves). Tangible database, for example, may include a hard-drive, solid state drive, flash memory, permanent memory such as ROM, magnetic, optical, semiconductor, or any other suitable type of storage component. Intangible database, for example, may include storages implemented by software.

The system can stock a combination of items including, without limitation, medications, tablets, vaccines, surgical tools and other consumable products. Such items are initially transferred into the system by way of a stocking procedure and are subsequently transferred out of the system for use by way of a transfer procedure. A stocking procedure and a transfer procedure are shown in FIG. 3A and FIG. 3B respectively. Bulk items, referred to herein as a pack, such as a package of ten syringes or a twenty-count box of medication tablets, can be stocked unopened and stored in the system e.g. on a tray. Individual items within the pack e.g. a single syringe, a single tablet or a single dosage, referred to herein as lower unit of measure (LUM), can subsequently be transferred from the system. The serial numbers of the packs and associated codes (e.g. product codes) related to the items can be stored upon stocking and used to track items as they are transferred. For example, the serial number and/or product codes can be stored on a 2D code on the pack and scanned with an optical scanner during stocking. The stocking and vending procedure prevent waste in the case that a pack is taken to serve the purpose of a LUM and allow the system to tightly track the chain of custody of the items. Furthermore, the serial numbers and/or product codes can be used to incorporate pack to LUM conversion so the items can be tracked from the pack level down to the LUM level, as discussed herein in more detail.

In some embodiments, a pack serial number is scanned upon stocking of the pack and the serial number and associated product codes are stored in the system. The associated product codes can correspond to the pack and/or the LUMs in the pack. In alternative embodiments, a pack a serial number can be scanned upon stocking and a separate LUM serial number can be scanned and stored later when the LUM is selected for removal. In alternative embodiments, the system may be pre-loaded with serial numbers and/or product codes i.e. scanning of the pack or LUM is not the first capture of the serial number and/or product code by the system. The serial numbers and product codes can be a unique identifier (e.g. an alphanumeric identifier), a SKU, a UPC, a lot number, date code, National Drug Code or other representation of information. Other item information, as described herein, can also be stored at the time the pack or LUM serial number and/or product code is scanned.

The system can be configured to implement pack to LUM conversion. The pack serial numbers can be associated with product codes corresponding to the LUMs in the pack. Therefore, LUMs as well as packs can be accounted for in the system e.g., in a database. In some embodiments, the LUM product codes are captured by the system when a pack is stocked (pack serial number scanned) and the system uses the product codes to keep track of the count of LUMs of a particular product code remaining in the system as LUMs are subsequently removed. Additionally or alternatively, the count of unopened packs stocked on the tray can be tracked. The user can, at the direction of the system, scan an unopened pack serial number, remove a LUM and return the remaining LUMs to the system. The database can then, using the serial number, mark the status of the scanned pack as unavailable and update the count of LUMs available by increasing the count of LUMs of the corresponding product code to the number of LUMs remaining in the pack. This configuration allows for tracking of LUMs even in case where the LUMs are not serialized. In alternative embodiments, the user may scan a LUM serial number when removing one or more LUMs from the system and the number of LUMs remaining in the system may be updated using the LUM serial number and/or product code associated with the LUM serial number i.e., the count in the database associated with the LUM serial number and/or product code can be updated. The advantages of the system incorporating pack to LUM conversion include reduction of waste because partially consumed packs can be placed back on the tray and tighter tracking because items are not only tracked at the pack level but at the LUM level. It is important to note that item count is not the only type of item information that may be updated when packs and LUMs are scanned. Other information such as location information can be updated as well to facilitate item tracking. In addition, because the system is capable of pack to LUM conversion, the tray can be used to store portions of a bulk item or pack and track the contents of the pack at the LUM level.

Referring to FIG. 3A, a stocking procedure is shown. At step 1, a user authenticates one or more user credentials via a tray management device to access the system. At step 2, the user stocks one or more unopened packs. The user scans the serial number of each pack to be stocked with the optical scanner and a database is updated with the serial number and associated product codes, both of which are read from a 2D code on the pack. In some embodiments, the database can be updated with other item information, as disclosed herein, in addition to the serial number and product codes. Such information can be retrieved from the system e.g., from a database or from a user input to a user interface. At step 3, the packs are placed on the platform and the total load on the platform is sensed by the weight sensors. The total load at the time of stocking can be stored in the database or in a tray management device for later retrieval. At step 4, the weight sensors detect any change in the total load on the platform and send an alert communicating the change to a remote device such as a tray management device or a remote server. These alerts can be displayed on a user interface used by another process in the system.

Referring to FIG. 3B, step 1 shows packs previously stocked on the platform. At step 2, a user accesses the system via a tray management device by entering one or more credentials. Once authenticated, the user enters a user selection via the tray management device for one or more desired items, which may be packs or LUMs. At step 3, the user removes each selected pack or LUM from the tray and scans the pack or LUM serial numbers with the optical scanner. The system verifies that the scanned pack or LUM corresponds to the user selection using the database. In some embodiments, in which the LUM does not have a serial number, the pack serial number can be scanned and a LUM product code can be retrieved using the pack serial number in order to verify the LUM. At step 5, if the user selected to remove LUM(s) as opposed to a pack, the user returns the excess LUM(s), if any, to the platform e.g., the user desires to obtain a single tablet of a particular medication from a twenty-count box. At step 6, the system verifies that the correct packs or LUM(s) were removed from the platform by using the total load on the platform sensed by the weight sensors and/or the database. Item information, such as item count, is updated in the database.

Figure 5:
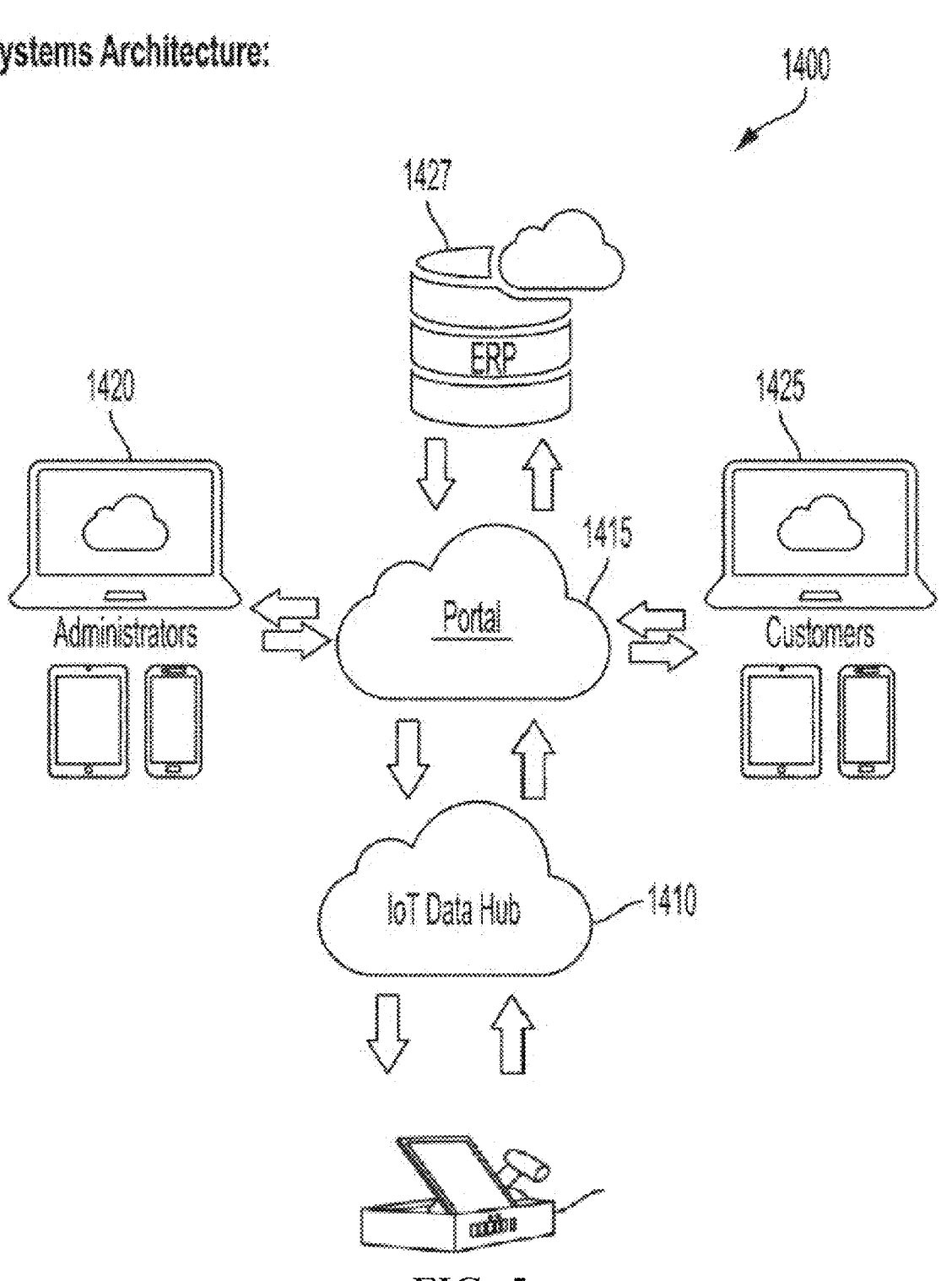
FIG. 5 depicts an illustrative system in accordance with some embodiments of the present invention.

FIG. 5 depicts an illustrative system architecture. The system 1400 includes one or more storage devices 1405, a computer hub 1410, a server 1415 implementing a portal, an administrator client device 1420, a customer client device 1425, tray management device 1406, and a management computer system 1427. The storage device 1405 can be a tray like the one shown in FIG. 1A. The storage device 1405 and/or the tray management device 1406 are configured to communicate (e.g., receive and transmit data) with the server 1415 via the computer hub 1410. The computer hub 1410 is configured to receive data and transmit data via a communications protocol. The computer hub 1410 is also configured to manage connectivity and data traffic between the server 1415 and the storage devices 1405. The computer hub 1410, for example, can be an IoT data hub. An IoT data hub can be an application implemented on a computing service over the Internet that is configured to handle communications with the storage devices 1405. An IoT data hub can also be a system that is implemented at the same location as where the storage devices 1405 are located or at a remote location. The system is configured to communicate with the storage devices 1405 and/or tray management device(s) 1406 via a private network such as WiFi, LAN, etc. The storage devices 1405 and tray management device 1406 are equipped with devices that are configured to communicate with the system. The IoT data hub may be configured to receive and aggregate data from the storage devices 1405 and/or tray management device 1406 periodically over the Internet or intranet such as every 5 minutes or at other frequencies. Storage devices 1405 can be connected via WiFi or LAN to other storage devices or may stand alone independently. Tray management device 1406 may be connected via WiFi or LAN to other tray management devices or may stand alone independently. The server 1415 that implements a portal is where all the data resides for managing the connected storage devices 1405 and tray management devices 1406. The server 1415 can be implemented on a cloud computing service over the Internet or on a system over a private network. The server 1415 may connect to a management computer system 1427 to facilitate movement of inventory through an integrated supply chain. The management computer system 1427, for example, may be an Enterprise Resource Planning (ERP) system. The server 1415 serves as the system of record for connected storage devices 1405 and/or tray management devices 1406 with regard to customer usage and demand, restocking, alert and trouble managed and storage device life cycle events. Administrators are individuals who are employed by the company deploying the storage devices 1405. Administrators access the server 1415 from their administrator client devices 1420 to access information regarding specific storage devices and interact with the storage devices 1405 and customers through various machine command protocols. For example, administrators can monitor the inventory of the storage devices, submit orders for items that are low on supplies or have no supplies, and issue invoices for the orders to the respective customers.

Administrators can also monitor the operating status of the storage devices and tray management devices, and check if any storage devices or tray management devices require adjustment, maintenance, or repair. For instance, administrators can observe that some storage devices have been set to operate at a higher than the maximum allowed temperature and inform the respective customers to lower their storage temperature. Administrators can note that some storage devices are operating in an alternative mode that relies on a backup battery, instead of the normal operating mode that relies on the primary source of power. Customers are individuals or entities that bought, leased, or otherwise have access to the storage device 1405 through a relationship with the company of the administrators. Customers likewise have access to reporting and other interactions with the server 1415 via their customer client devices 1425. Customers can also monitor the operating status of the storage devices and can place orders with human intervention or have orders placed automatically based on usage. For example, the tray management device may instruct the customer to enter the order number from the user interface and the tray management device. Administrators and customers can control and interact with the storage devices or tray management devices from their respective client devices that are remote from the location of the storage devices or over a network or Internet. Administrators and customers can create their respective accounts (e.g., username and password) in order to access the portal. A client device may be a desktop computer, laptop computer, a mobile computer, a tablet computer, a cellular device, a smartphone, a personal digital assistant (PDA), or any other computing devices having a microprocessor and memory.

Figure 6:
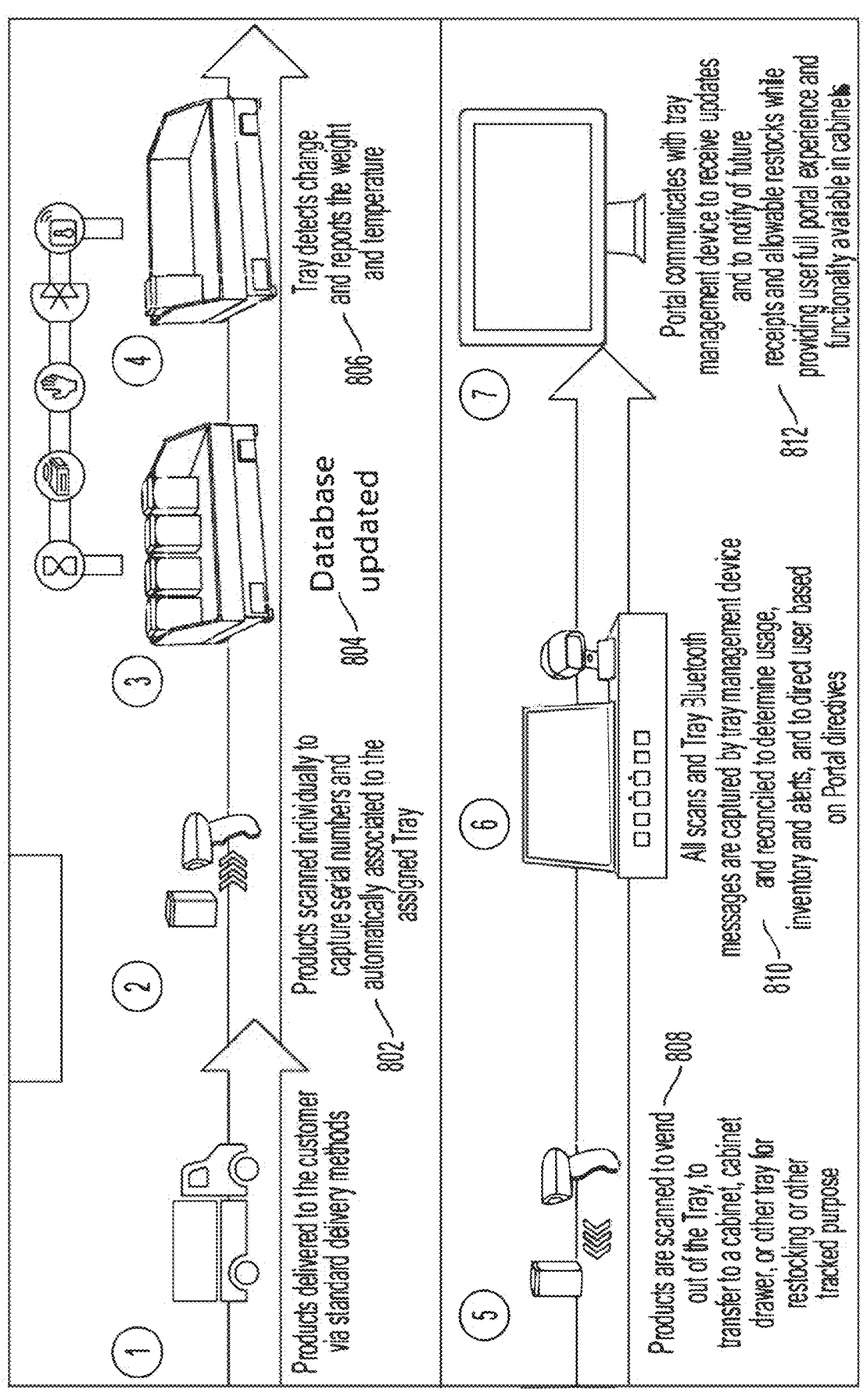
FIG. 6 depicts an illustrative method related to some aspects of system or tray operation in accordance with some embodiments of the present invention.

FIG. 6 illustrates a process and related system or device configurations. Product can be delivered to customers based on various triggers such as an order or regular delivery. At step 802, products delivered to the customer can be scanned using an optical scanner. The products can arrive in packs of bulk items such as ten-count boxes of syringes and have a serial number and/or product code stored in a 2D code on the pack. When the serial numbers and/or product codes are scanned they are stored in a database. In some embodiments, the scanning of the pack at step 802 is the first capture of the serial number and/or product code in the database. In alternative embodiments, the serial number and/or product code is already captured in the database.

At step 804, the database is updated with information, including but not limited to, product name, inventory count, manufacturer, lot number, date of manufacture, date and time information, medical facility name or address, name of person having custody (scanning item into system), tray ID (of the tray associated with the item by the system), room number (where the tray is located), sensor readings, item expiration date and item storage conditions.

Location information such as tray ID and room number can be used by the system to facilitate the user in locating a desired item in a system that incorporates multiple trays. For example, the system can communicate to a user via a tray management device the tray at which the selected item is available by sending an alert via a tray management device containing the tray ID and/or room number. This configuration is useful in the event that the user scans an item for removal and that item is expired, was not stored at the proper temperature conditions, is out of stock on a particular tray or is otherwise unavailable in one or more locations in the system.

At step 806, one or more desired products is removed from the tray. In response to the tray sensing the removal of one or more products the tray can transmit a message wirelessly to the tray management device comprising sensed information such as the weight output or temperature reading from the corresponding sensor. The weight output can be used to verify the products removed as discussed below.

At step 808, the customer scans the removed product(s). If the customer elects to remove an entire pack, the customer scans the pack serial number. If the customer elects to remove a LUM the customer scans the LUM serial number if available. The scans are used to update the database. If the LUM serial number is not available (the LUM doesn't have a serial number), the system uses pack to LUM conversion, as discussed previously, to update the database.

At step 810, tray management device (and supporting systems if desired) is configured to capture the product scans and use messages from the tray to reconcile the current stock of inventory and determine usage of products by the customer.

At step 812, the system is configured to provide a portal to the customer (e.g., see FIG. 7) that is configured to provide the customer with the information about the stocked items, status of inventory, and delivery of products.

The storage of information such as time and place of stocking and removal, location information (tray ID, room number, medical facility) and user information (name of person or entity who stocked and/or removed a product) in association with product serial numbers and/or product codes facilitates tracking of the chain of custody of packs and LUMs. In some embodiments, packs may be tracked by updating the location information, user information and time and place of stocking or removal or combinations thereof associated with a pack serial number every time a pack is scanned for stocking or removal. Additionally or alternatively, a LUM may be tracked by updating location information, user information and time and place of removal or combinations thereof associated with a LUM serial number every time a LUM is scanned for removal. In alternative embodiments, LUMs can be tracked without scanning by performing pack to LUM conversion and then updating location information, user information and time and place of removal and combinations thereof associated with LUM product codes every time a user elects to remove one or more LUMs from the system.

Figure 7:
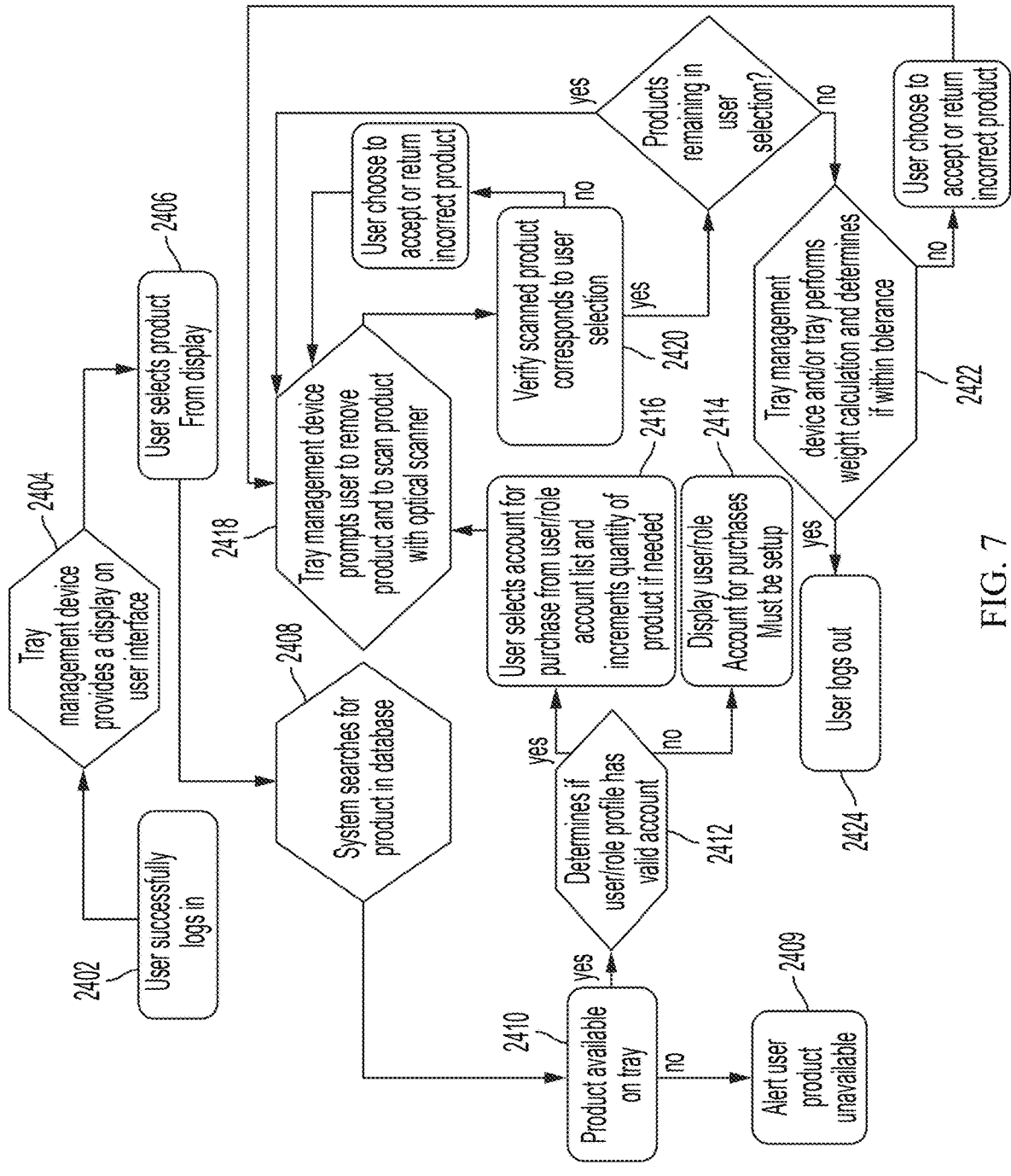
FIG. 7 depicts an illustrative flow chart in accordance with some embodiments of the present invention.

With reference now to FIG. 7, the system using the trays can be configured in structure and operation to implement security and inventory management that can provide significant benefits to users, facilities, and cabinet providers. Flow chart 2400 of FIG. 7 can be implemented using the software and hardware described herein. At step 2402, the tray management device, by way of a user interface, can provide the user (a user that has physically approached the device) with the ability to login by providing one or more credentials and in response, the tray management device can check the information and authenticate the user.

At step 2404, the tray management device can generate a display, via the user interface, that provides the user with an interactive option to select a product (such as a particular packaged medical product or device). This can be provided by the interface by providing a keyword searching tool, product browsing tool, or other technique. At step 2406, the selection of a product by the user can be received via the user interface (e.g., the user using a touch screen or pointing device on the interface to select a product and quantity).

At step 2408, in response to the selection of a product by the user, the tray management device searches, using the database, for the product to determine whether the tray is stocked with that product. An algorithm can be implemented to prioritize which available item is selected from the database.

At step 2410, in response to the identifying an item of that product is available on the tray, the process proceeds to step 2412. If an item of that product is not available, the process proceeds to step 2409 and the tray management device sends the user a message via the user interface indicting that that product is unavailable. At step 2412, the tray management device can determine whether the login user has authorization and a valid account to carry out the transaction for that item. At step 2414, if the account is not valid or if the account of that user does not have the authorization for that product, the process can be terminated. At step 2416, if the account is valid and if implemented and the level of authorization is sufficient, the system can perform the related process with the user's account and update the product count.

At step 2418, the tray management device (in response to the above) directs the user, via the user interface, to remove the selected product from the tray and to scan the serial number of the product, if the product is serialized. At step 2420, the tray management device verifies that the serial number of the scanned product corresponds to the user selection. If a discrepancy is detected, the tray management device can recommend a manner of correction to the user e.g., allow the user to opt to return the removed item to the tray and select a different (correct) item or to accept the incorrect item. If the user opts to accept the incorrect item, the system can take into account this change when updating product statuses in the database later. The tray management device can be configured to provide a prompt or other process feature that prevents the tray management device from proceeding to logging out the user or moving past the error unless the user interacts to correct the mistake or accepts the removal of a different product. If desired, the tray management device can send an alert to other devices if the user does not address the error (e.g., walks away from the tray with the item). Interactions between the user and the tray management device can be captured in one or more log files.

At step 2422, the weight calculation is performed to verify the correct product(s) were removed. In this way the system implements multiple product authentication layers using the scanned serial numbers of the products removed and weight sensed by the weight sensors. The weight calculation can include a first value defined as the difference in the total load sensed on the platform at step 2402 and the total load sensed on the platform at step 2422. The first value can be compared to a second value. The second value can be determined by the tray management device and/or the tray using the database. For example, the tray management device can retrieve one or more expected weights from the database and subtract the expected weights from the total load on the platform at step 2422 to determine the second value. The expected weights can be a weight derived from an external source such as the manufacturer's data sheet or from a measurement by the weight sensors at an earlier point in time. A tolerance can also be factored into the weight calculation. The tolerance can be a value, also stored in the database, that accounts for tare weight of the weight sensing area, tools, manuals, packaging and other items auxiliary to the products stored on the tray. The tolerance can also account for any structures enclosing the platform configured to facilitate in storing items on the platform such as walls or a bin. The system can use the tolerance to determine if the output of the weight calculation is acceptable or if an anomaly exists. For example, the system can determine if the difference between the first value and the second value falls within the tolerance.

If an anomaly is detected in the weight calculation, the tray management device generates an error and communicates (such as by displaying an error message using the interface on the monitor) that a determination was made the removed item is not correct or proper. The tray management device can prompt the user via the user interface to return the item or can prompt the user to accept the different product that may have been taken. If via the interface, the user accepts the different product, the corresponding information is updated in the database (e.g., item count or serial number). Thus, the tray management device can generate an error and/or provide an option to accept the mistake before the user can complete the item removal process. The tray management device can be configured to provide a prompt or other process feature that prevents the tray management device from proceeding to logging out the user or moving past the error unless the user interacts to correct the mistake or accepts the removal of a different product. If desired, the tray management device can send an alert to other devices if the user does not address the error (e.g., walks away from the tray with the item).

If no anomaly is detected in the weight calculation, the user is permitted to log out at step 2424. The weight calculation and/or associated output, such as an error message, can be captured in a log file.

Both the tare weight and the timing of the weight calculation facilitate accurate tracking by the system. Because the tare weight accounts for auxiliary items like packaging, the user can, for example, remove a pack from the tray, remove the required LUMs, discard the packaging and return the remaining LUMS to the tray without triggering an error in the system. The system performing the weight calculation after the user returns the unneeded LUMs to the platform also circumvents any errors arising from the user removing excess LUMs from the tray such as when the user removes a pack in order to retrieve a single LUM.

For the sake of brevity and clarity, the present description may have been written without specific discussion referencing software or hardware (equipment). It should be understood that software and/or hardware of the tray, cabinet or system are configured to provide the described features or functionality such as to provide the described operational capability. This is to affirmatively explain that the tray, system, cabinet, or corresponding element is configured to provide the described capability.

A computer station refers to the cabinet or tray management device as illustratively described herein.

It should be understood that variations, clarifications, or modifications are contemplated. It should also be understood by one of ordinary skill in the art that features, processes, or elements described in various context or portions in this application can be combined to provide variations (various combinations) that are within the scope. For example, in some portions, a scan or an optical reader is implemented as part of stocking and/or removing products for us but other embodiments are contemplated. It would be understood that features described herein to provide corresponding operation functionality as part of the cabinet, system, or process can be substantially, substantially only, primarily, consisting of, or consisting essentially of that feature for providing that operational functionality. Applications of the technology to other fields are likewise contemplated.

It is understood from the above description that the functionality and features of the systems, devices, or methods of embodiments of the present invention include generating and sending signals to accomplish the actions.

Exemplary systems, devices, and methods are described for illustrative purposes. Further, since numerous modifications and changes will readily be apparent to those having ordinary skill in the art, it is not desired to limit the invention to the exact constructions as demonstrated in this disclosure. Accordingly, all suitable modifications and equivalents may be resorted to falling within the scope of the invention.

Thus, for example, any sequence(s) and/or temporal order of steps of various processes or methods (or sequence of device connections or operation) that are described herein are illustrative and should not be interpreted as being restrictive. Accordingly, it should be understood that although steps of various processes or methods or connections or sequence of operations may be shown and described as being in a sequence or temporal order, but they are not necessarily limited to being carried out in any particular sequence or order. For example, the steps in such processes or methods generally may be carried out in various different sequences and orders, while still falling within the scope of the present invention. Moreover, in some discussions, it would be evident to those of ordinary skill in the art that a subsequent action, process, or feature is in response to an earlier action, process, or feature.

It is also implicit and understood that the applications or systems illustratively described herein provide computer-implemented functionality that automatically performs a process or process steps unless the description explicitly describes or would primarily be understood to involve user intervention or manual operation (e.g., determining nest configuration in a drawer is automatically performed by the cabinet, detecting a broken pattern is automatically performed by the cabinet, etc.).

It should be understood that claims that include fewer limitations, broader claims, such as claims without requiring a certain feature or process step (e.g., removing a feature or step) in the appended claim or in the specification, clarifications to the claim elements, different combinations, and alternative implementations based on the specification, or different uses, are also contemplated by the embodiments of the present invention.

The words "can" or "may" are used to communicate or clarify that this is one option and other options or variations are contemplated. This is not to say that if such a word is not used, it is being communicated that this only implementation.

It should be understood that combinations of described features or steps are contemplated even if they are not described directly together or not in the same context.

The terms or words that are used herein are directed to those of ordinary skill in the art in this field of technology and the meaning of those terms or words will be understood from terminology used in that field or can be reasonably interpreted based on the plain English meaning of the words in conjunction with knowledge in this field of technology. This includes an understanding of implicit features that for example may involve multiple possibilities, but to a person of ordinary skill in the art a reasonable or primary understanding or meaning is understood.

It is intended that the specification and examples be considered as exemplary only, with a true scope being indicated by the claims and their equivalents.

What is claimed is:

1. A flex weight sensing tray system that stores packaged medicine or other regulated healthcare related devices for taking using an optical scanner, comprising:
   a portable open-top tray comprising an enclosed housing and a platform positioned above housing and configured to store a combination of items including packs and LUMs, wherein the platform includes a solid flat surface that is adapted to be open for access by hand of a user so that a user can remove an item from the platform and a weight sensing area having one or more weight sensors, wherein the weight sensor is configured to sense the weight of a total load on the platform;
   an optical scanner configured to scan information; and
   a processor, memory, wireless communications circuit and computer readable instructions stored in memory, wherein the computer readable instructions configure the processor and wireless communications circuit to perform the steps comprising:
   storing scanned information from one or more packs in a database, wherein the scanned information includes one or more serial numbers and product codes corresponding to the one or more packs and one or more serial numbers and product codes corresponding to each LUM in the one or more packs;
   communicate to a user, via a user interface, an option to authenticate one or more credentials of the user;
   in response to authenticating the user, permit the user, via the user interface, to enter a user selection to obtain one or more items from the platform and prompt the user to remove the one or more of items in the user selection from the platform;
   receive, via the optical scanner, one or more serial numbers corresponding to the one or more removed items;
   retrieve one or more expected weights from the database corresponding to the one or more removed items;
   calculate a first weight and a second weight using the database and the one or more weight sensors;
   permit the user interaction to obtain the one or more removed items to proceed without error when it is determined that (a) the one or more serial numbers corresponds to the user selection and (b) a difference between the first weight and the second weight falls within a tolerance; and
   update in the database one or more statuses of the one or more removed items in order to track removal of items from the tray.

2. The system of claim 1, wherein the database is stored on a remote server.

3. The system of claim 1, wherein the tray further comprises an enclosure enclosing the processor.

4. The system of claim 1, wherein the processor is located in a tray management device.

5. The system of claim 4, wherein the tray management device is a tablet.

6. The system of claim 5, wherein the user interface is located in the tray management device.

7. The system of claim 1, wherein the status is the current count of the one or more removed items.

8. The system of claim 1, wherein the system is configured to communicate to the user, via the user interface, whether an item is available, and if available, to communicate to the user to scan the item out of the tray.

9. The system of claim 1, wherein the one or more product codes corresponding to each LUM are a National Drug Code.

10. The system of claim 1, wherein the tolerance includes manuals, tools, packaging and other ancillary items that are stored on the platform.

11. The system of claim 1, wherein the tolerance includes the tare weight of the weight sensing area.

12. The system of claim 1, wherein the tray further comprises one or more walls enclosing the platform.

13. The system of claim 1, wherein one of the one or more items removed is a first LUM from a pack and at least one of the one more statuses updated in the database is a count of LUMs remaining in the pack following removal of the first LUM by the user.

14. The system of claim 1, further comprising a temperature sensor, wherein the temperature sensor is configured to transmit a report on temperature to the processor.

15. The system of claim 1, wherein the database is configured to store information that facilitates tracking of the chain of custody of the one or more removed products.

16. The system of claim 13, wherein the pack is unopened prior to removal of the first LUM by the user.

\* \* \* \* \*